(12) United States Patent
Ogasawara et al.

(10) Patent No.: US 7,588,538 B2
(45) Date of Patent: Sep. 15, 2009

(54) ULTRASONIC DIAGNOSTIC EQUIPMENT AND IMAGE PROCESSING APPARATUS

(75) Inventors: Yoichi Ogasawara, Nasu-gun (JP); Tetsuya Kawagishi, Kuroiso (JP); Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 620 days.

(21) Appl. No.: 10/937,663

(22) Filed: Sep. 10, 2004

(65) Prior Publication Data
US 2005/0059893 A1 Mar. 17, 2005

(30) Foreign Application Priority Data
Sep. 11, 2003 (JP) ............................. 2003-319885

(51) Int. Cl.
*A61B 8/00* (2006.01)
(52) U.S. Cl. ................. 600/454; 600/437; 600/458
(58) Field of Classification Search .................. 600/454
See application file for complete search history.

(56) References Cited

U.S. PATENT DOCUMENTS

| | | | | |
|---|---|---|---|---|
| 5,735,281 | A * | 4/1998 | Rafter et al. ................. | 600/458 |
| 5,873,829 | A * | 2/1999 | Kamiyama et al. ........... | 600/443 |
| 5,947,904 | A * | 9/1999 | Hossack et al. .............. | 600/458 |
| 5,957,845 | A * | 9/1999 | Holley et al. ................ | 600/440 |
| 6,077,225 | A * | 6/2000 | Brock-Fisher .............. | 600/439 |
| 6,080,107 | A * | 6/2000 | Poland ........................ | 600/458 |
| 6,086,540 | A * | 7/2000 | Bonneville et al. .......... | 600/458 |
| 6,149,597 | A * | 11/2000 | Kamiyama .................. | 600/458 |
| 6,171,246 | B1 | 1/2001 | Averkiou et al. | |

(Continued)

FOREIGN PATENT DOCUMENTS

EP 1 314 398 A1 5/2003

(Continued)

OTHER PUBLICATIONS

Kevin Wei, et al., "Quantification of Myocardial Blood Flow With Ultrasound-Induced Destruction of Microbubbles Administered as a Constant Venous Infusion", Circulation, vol. 97, No. 5, Feb. 10, 1998, pp. 473-483.

(Continued)

*Primary Examiner*—Brian Casler
*Assistant Examiner*—Crystal I Leach
(74) *Attorney, Agent, or Firm*—Oblon, Spivak, McClelland, Maier & Neustadt, P.C.

(57) ABSTRACT

After the establishment of the saturation state of a contrast medium which has flowed into a subject for scanning inside a patient given the contrast medium, scan is performed under a high acoustic pressure adapted to break the bubbles of the contrast medium, so as to refresh the section for the scanning, and to acquire the maximum value of echo signal intensities. Subsequently, scans by ultrasounds under a low acoustic pressure or a medium acoustic pressure which does not break the contrast medium are carried out a plurality of times at different timings, thereby to execute a scan sequence for acquiring in-vivo information necessary for a TIC analysis. Data obtained by the scans are analyzed in a blood-flow-index estimation unit, and are displayed in a predetermined scheme.

27 Claims, 9 Drawing Sheets

U.S. PATENT DOCUMENTS

| | | | |
|---|---|---|---|
| 6,245,019 B1 * | 6/2001 | Kamiyama | 600/458 |
| 6,315,730 B1 * | 11/2001 | Hoff et al. | 600/458 |
| 6,340,348 B1 * | 1/2002 | Krishnan et al. | 600/447 |
| 6,436,045 B1 * | 8/2002 | Rafter et al. | 600/447 |
| 6,436,049 B1 * | 8/2002 | Kamiyama et al. | 600/458 |
| 2003/0092991 A1 * | 5/2003 | Sehgal | 600/458 |
| 2005/0059893 A1 | 3/2005 | Ogasawara et al. | |
| 2005/0267371 A1 | 12/2005 | Ogasawara | |

FOREIGN PATENT DOCUMENTS

| | | |
|---|---|---|
| JP | 2003-61959 | 3/2003 |
| WO | WO 98/47533 | 10/1998 |

OTHER PUBLICATIONS

U.S. Appl. No. 12/237,683, filed Sep. 25, 2008, Kamiyama et al.

* cited by examiner

ULTRASONIC DIAGNOSTIC EQUIPMENT AND IMAGE PROCESSING APPARATUS

CROSS-REFERENCE TO RELATED APPLICATIONS

This application is based upon and claims the benefit of priority from prior Japanese Patent Application No. 2003-319885, filed Sep. 11, 2003, the entire contents of which are incorporated herein by reference.

BACKGROUND OF THE INVENTION

1. Field of the Invention

The present invention relates to ultrasonic diagnostic equipments wherein, in a mode where ultrasounds which are based on a low acoustic pressure that does not burst the bubbles of a contrast medium are transmitted when the contrast medium is given and where the intensity changes of the ultrasounds are observed, the bubbles are broken by transmitting a high acoustic pressure capable of bursting the bubbles in a moment, an index about blood flow information is estimated on the basis of the data of an echo signal group before and after the breaking of the bubbles, and the estimated information is offered to an observer.

2. Description of the Related Art

In an ultrasound contrast examination, a contrast medium which is made of shell less micro bubbles or shelled ones formed of sugar or fat is used, and a blood flow movement is observed by utilizing the enhancement of echo signals based on the contrast medium, thereby to diagnose the function of an internal organ, to differentially diagnose a tumor or to diagnose the degree of progression of the tumor, or to follow up a therapeutic effect. Contrast media which are currently permitted to be injected into blood from veins for the purpose of ultrasonic diagnoses, within the State of Japan, are of the property of generating intense signals when the contrast media are caused to collapse and disappear by ultrasound transmission. The contrast medium of this property can produce a greater contrasting effect by positively breaking bubbles. However, each time the bubbles are broken for imaging, the contrasting effect is shortened. It is therefore impossible to observe intensity changes repeatedly with one time of contrast medium injection. The contrast medium must be sometimes injected anew, depending upon the contents of the diagnosis. When the quantity of injection increases in this manner, a patient is forced to bear a physical burden and an economical burden correspondingly.

Meanwhile, in recent years, bubbles which generate intense nonlinear signals without being broken by low-acoustic-pressure ultrasounds have been developed as ultrasound contrast media of next generation (hereinbelow, also termed "next-generation contrast media"). The next-generation contrast medium presents the enhancement of the signals under a low acoustic pressure without causing the bubbles to collapse and disappear as in the conventional contrast medium, so that it permits a region of interest to be repeatedly diagnosed. Incidentally, at present, the next-generation contrast media are at the stage of clinical drug trials within the State of Japan. In contrast, they have already been authorized and employed at clinical sites in some oversea regions.

Most suited as an imaging method which employs the bubbles of such a next-generation contrast medium is a technique which does not directly apply the conventional method of causing the bubbles to collapse by transmitting ultrasounds under the high acoustic pressure, but which transmits the ultrasounds under a low acoustic pressure that does not cause the bubbles to collapse, and which utilizes the reflected waves of the transmitted ultrasounds. The manufacturers of ultrasonic diagnostic equipments have developed equipments capable of coping with the next-generation contrast media, and have already put these equipments into the market.

On the other hand, as an imaging technique employing the ultrasound contrast medium has been established in recent years, it has been vigorously attempted to offer, not only an image requiring a subjective judgment for a diagnosis, but also objective quantitative information. The "objective quantitative information" is, for example, that quantitative information on a blood flow which is obtained from the changes of signal enhancement versus time as are based on the contrast medium. Owing to such quantitative information, it is possible to make the diagnosis of the function of an internal organ or the differential diagnosis of a tumor and the diagnosis of the degree of progression of the tumor more objectively.

When the quantitative information is to be acquired using the conventional ultrasound contrast medium (which is not of the next generation), high-acoustic-pressure ultrasounds (ultrasounds for imaging) need to be transmitted a plurality of times with transmission intervals changed. Ultrasound scans are performed many times at the different transmission intervals in this manner, for the following reason: as already stated, the micro bubbles forming the conventional ultrasound contrast medium are caused to collapse and disappear by the transmission of the high-acoustic-pressure ultrasounds for imaging, and the bubbles (the contrast medium) within a scanning plane are broken by each time of transmission. In order to collect data corresponding to various elapsed times, therefore, ultrasound transmission operations in which the respective time periods are individually caused to lapse are required. In a case, for example, where the data of a TIC (Time Intensity Curve) till 20 seconds sampled and collected at time intervals of one second, a time period of $1+2+3+ \ldots +18+19+20=210$ seconds is expended.

Figures 11A, 11B:
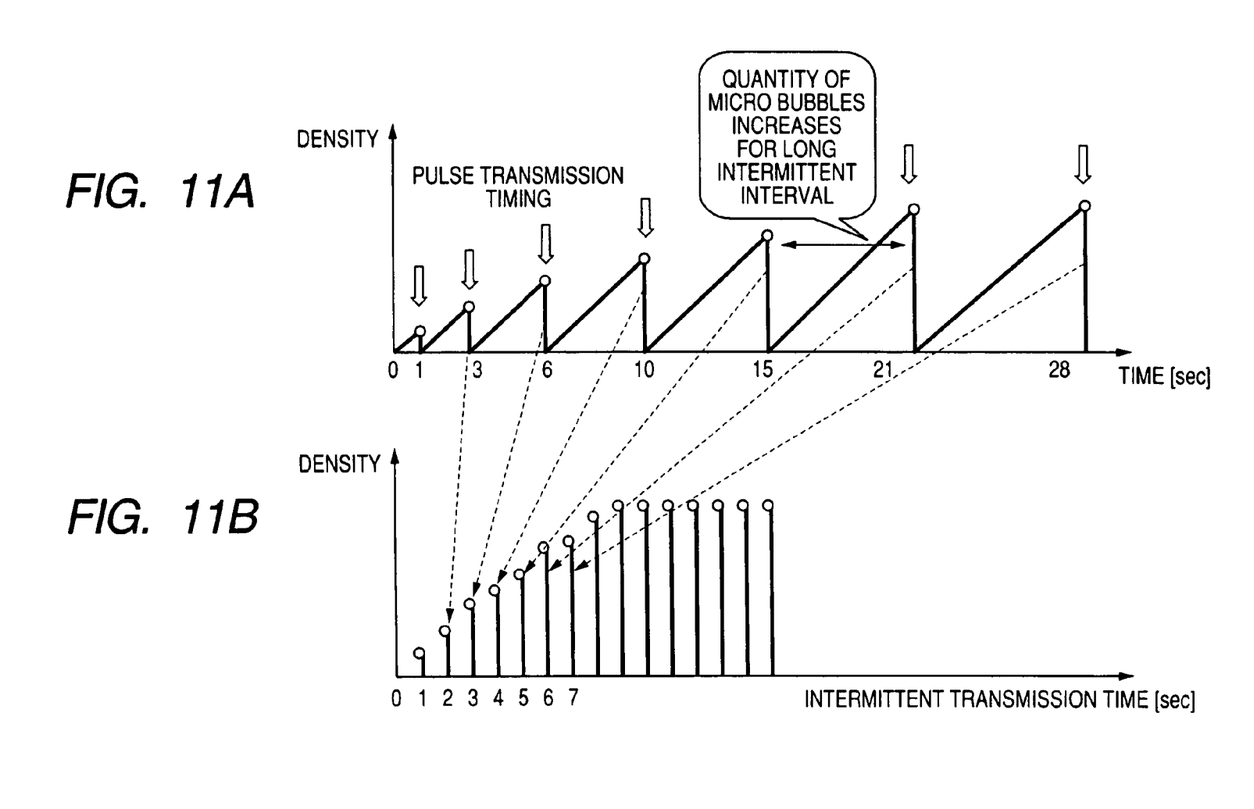

FIG. 11A is a diagram showing a scan sequence example in the case where high-acoustic-pressure ultrasounds are transmitted with transmission intervals changed. Echo signals obtained by ultrasound transmission conforming to the sequence are plotted in correspondence with the respective time intervals as shown in FIG. 11B. A function thus found becomes a curve (time intensity curve) indicative of a state where a contrast medium is accumulated with the lapse of time. A doctor can obtain objective quantitative information on the basis of the curve.

However, problems as stated below by way of example are involved in acquiring the objective quantitative information with the ultrasound contrast medium.

In the first place, operator such as a doctor must continue to hold an identical section during the intermittent transmission with the time intervals changed. This is difficult due to the motions of internal organs in a scanning mode, and from a technical viewpoint.

Secondly, breath holding for a long time period (which is generally said to be about 10-15 seconds though opinions differ depending upon doctors and technicians) must be required of a patient in order to suppress the organic motions in, for example, the abdominal region. This becomes a heavy burden particularly on the elderly, patients of low physical strengths, and others.

Thirdly, in a case where the section of data acquired at the different time intervals has shifted due to a two-dimensional or three-dimensional movement, the reliability of the quantitative information lowers.

Incidentally, as disclosed in, for example, JP-A-2003-61959, a scanning time period in such problems involved in the acquisition of the quantitative information can be shortened to a certain degree by contriving the scan sequence of the high-acoustic-pressure ultrasounds. From the viewpoint of lightening the burdens on the operator and the person to-be-photographed, however, it is desired to shorten the scanning time period still further.

BRIEF SUMMARY OF THE INVENTION

The present invention has been made in view of the above circumstances, and has for its object to provide ultrasonic diagnostic equipments which are capable of ultrasound scans by techniques adapted to satisfactorily exploit the characteristics of next-generation contrast media, whereby burdens on a operator and a person to-be-scanned in a scanning mode can be lightened.

According to an aspect of the present invention, there is provided an ultrasonic diagnostic equipment comprising an ultrasonic probe which transmits and receives ultrasounds to and from a subject for scanning within a patient given a contrast medium; a drive unit which generates a drive signal for driving the ultrasonic probe, and which feeds the drive signal to the ultrasonic probe; a control unit which controls the drive unit on the basis of a sequence for collecting changes-versus-time of a contrast medium density within the subject for scanning, the sequence being formed so that, after the contrast medium flowing into the subject for scanning has substantially fallen into a saturation state, first ultrasounds at an intensity at which the contrast medium is broken may be transmitted from the ultrasonic probe, and that, at different timings after the transmission of the first ultrasounds, second ultrasounds at an intensity at which the contrast medium is not broken may be transmitted from the ultrasonic probe at least twice; an analysis unit which analyzes information on a blood flow of the subject for scanning, on the basis of ultrasonic echoes received by the ultrasonic probe, and which thereby obtains an analytical result; and a display unit which displays the analytical result.

According to another aspect of the present invention, there is provided an image processing apparatus comprising a memory which stores therein echo signals obtained in accordance with a scan sequence for collecting changes-versus-time of a contrast medium density within a subject for scanning inside a patient, the scan sequence being formed so that, after a contrast medium flowing into the subject for scanning has substantially fallen into a saturation state, first ultrasounds at an intensity at which the contrast medium is broken may be transmitted, and that, at different timings after the transmission of the first ultrasounds, second ultrasounds at an intensity at which the contrast medium is not broken may be transmitted at least twice; an analysis unit which analyzes information on a blood flow of the subject for scanning, on the basis of the echo signals stored in the memory, and which thereby obtains an analytical result; and a display unit which displays the analytical result.

BRIEF DESCRIPTION OF THE SEVERAL VIEWS OF THE DRAWING

FIG. 11A is a diagram showing a scan sequence example in the case where high-acoustic-pressure ultrasounds are transmitted with transmission intervals changed, while FIG. 11B is a diagram showing a time intensity curve which has been drawn by plotting echo signals obtained by ultrasound transmission conforming to the sequence in FIG. 11A.

DETAILED DESCRIPTION OF THE INVENTION

Now, the first and second embodiments of the present invention will be described with reference to the drawing. By the way, in the ensuing description, identical signs will be assigned to constituents having substantially the same functions and configurations, and the constituents shall be repeatedly described only in necessary cases.

Incidentally, the embodiments shall exemplify cases of using a contrast medium of next-generation type. Besides, the "contrast medium of the next-generation type" shall signify a "contrast medium which can attain a satisfactory signal enhancement effect even when contrast medium bubbles are not broken, in an ultrasonic diagnosis", while a "contrast medium of conventional type" shall signify a "contrast medium which cannot attain a satisfactory signal enhancement effect unless contrast medium bubbles are broken, in an ultrasonic diagnosis". Mentioned as a typical example of the next-generation contrast medium is a contrast medium formed of bubbles whose shells are made of fat or a surfactant and in which the air or fluorocarbon being an inert gas is contained in the shells.

First Embodiment

Figure 1:
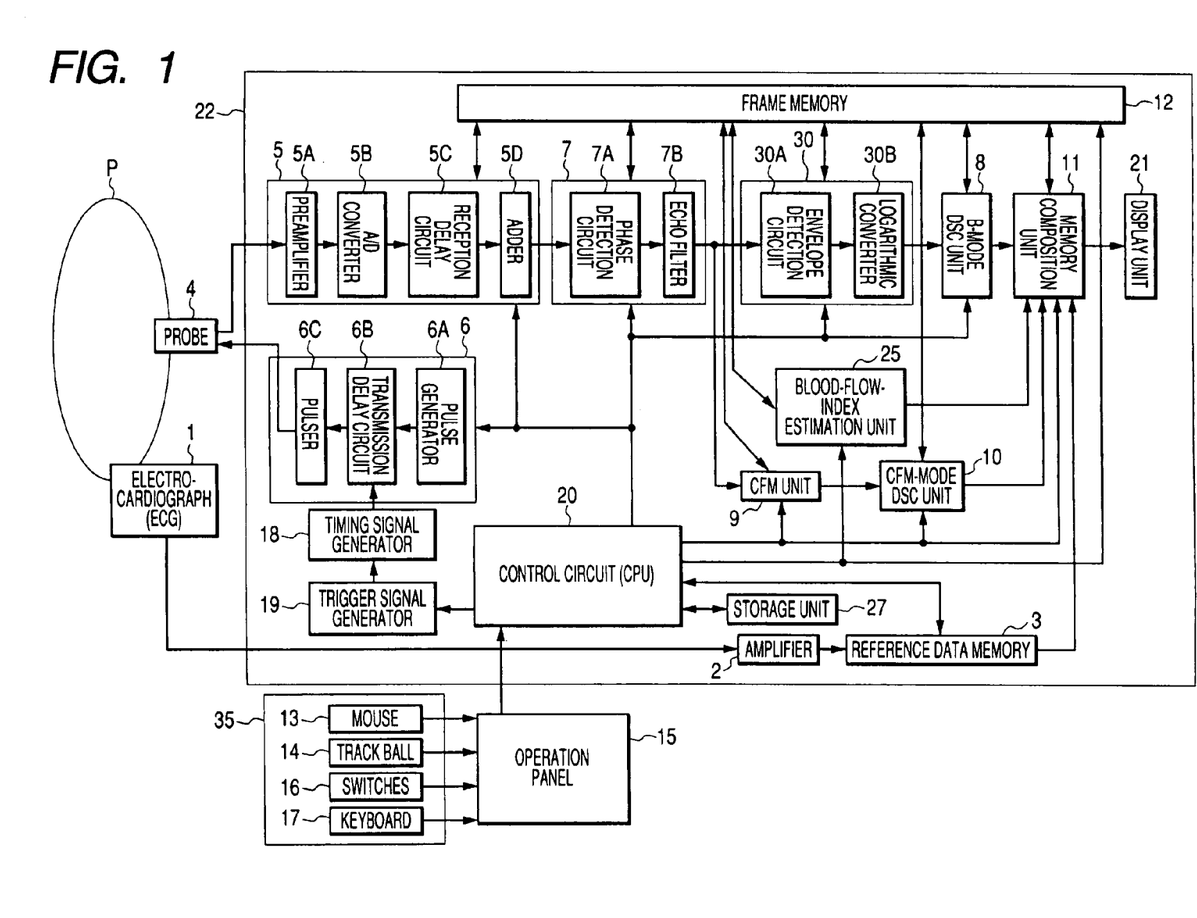
FIG. 1 shows a block arrangement diagram of an ultrasonic diagnostic equipment embodying the present invention.

The configuration of an ultrasonic diagnostic equipment according to the first embodiment will be described with reference to FIG. 1. The figure shows a block arrangement diagram of the ultrasonic diagnostic equipment. As shown in FIG. 1, the ultrasonic diagnostic equipment is configured of an electro-cardiograph (ECG: ElectroCardioGraph) 1, an ultrasonic probe 4, the equipment proper 22, an operation panel 15, and an input device 35. The constituents of the equipment will be explained below.

The electrocardiograph (ECG) 1 measures a graph in which a temporal variation in the electric phenomenon of the heart of a patient P is recorded, that is, an electrocardiogram. An electrocardiac waveform signal detected by the electrocardiograph 1 is sent to a reference data memory 3 through an amplifier 2. If necessary, the signal is sent to a display unit 21 through a memory composition unit 11 so as to be displayed as an electrocardiac waveform.

The ultrasonic probe 4 has a plurality of piezoelectric vibrators which are acoustic/electric reversible transducers made of piezoelectric ceramics or the like. The plurality of piezoelectric vibrators are arrayed, and are disposed at the distal end of the probe 4.

The operation panel 15 is connected to the equipment proper 22, and it is furnished with the input device 35 (including a mouse 13, a track ball 14, switches 16 and a keyboard 17) for accepting various directions, instructions and information from an operator into the equipment proper 22, and for performing the settings of a region of interest (ROI), etc. Incidentally, the switches 16 of the input device 35 include a mode changing switch, an image quality adjusting switch, an image saving switch and a measurement start switch, and besides, a switch for starting a quantitative information analysis (TIC analysis) as will be stated later. The operator operates the switches at suitable timings, whereby he/she can automatically execute a series of operations conforming to a sequence for the TIC analysis; scan, data saving, the analysis (estimation) of a blood flow index, and the display of an analytical result.

With a control circuit (CPU) 20 as the control center of the whole system, the equipment proper 22 includes the amplifier 2, a B-mode unit 30, an ultrasound reception unit 5, an ultrasound transmission unit 6, a receiver unit 7, a B-mode digital scan converter (DSC) unit 8, a color flow mapping (CFM) unit 9, a CFM-mode DSC unit 10, the memory composition unit 11, a frame memory 12, a timing signal generator 18, a trigger signal generator 19, the display unit 21, a blood-flow-index estimation unit 25, and a storage unit 27.

The ultrasound transmission unit 6 and the ultrasound reception unit 5 are connected to the ultrasonic probe 4.

The ultrasound transmission unit 6 includes a pulse generator 6A, a transmission delay circuit 6B and a pulser 6C.

The pulse generator 6A recurrently generates rate pulses at a rate frequency fr Hz of, for example, 5 kHz (period; 1/fr second). The rate pulses are distributed in the number of channels, and are sent to the transmission delay circuit 6B. The transmission delay circuit 6B focuses ultrasounds into the shape of beams, and gives the individual rate pulses delay times which are necessary for determining a transmission directivity. Incidentally, a trigger pulse from the trigger signal generator 19 is fed as a timing signal to the transmission delay circuit 6B through the timing signal generator 18. The pulser 6C impresses a voltage pulse on the probe 4 every channel at a timing at which the rate pulses have been delivered from the transmission delay circuit 6B. Thus, the ultrasound beams are transmitted to the patient P.

Reflected waves which have been reflected from the discontinuity plane of an acoustic impedance within the patient P, are received by the probe 4. Echo signals which are outputted from the probe 4 every channel, are accepted into the ultrasound reception unit 5.

The ultrasound reception unit 5 includes a preamplifier 5A, an A/D converter 5B, a reception delay circuit 5C and an adder 5D. The preamplifier 5A amplifies the echo signals accepted into the ultrasound reception unit 5 through the probe 4, every channel. Delay times necessary for determining a reception directivity are given to the amplified echo signals by the reception delay circuit 5C, and the resulting echo signals are added up by the adder 5D. Owing to the addition, a reflection component from a direction corresponding to the reception directivity of the echo signals is emphasized. The overall directivity of the ultrasound transmission and reception is determined by the reception directivity and the transmission directivity. The overall directivity is usually called "scan lines".

The receiver unit 7 subjects the echo signals delivered from the ultrasound reception unit 5, to phase detection by a phase detection circuit 7A, so as to extract signals of desired frequency band by an echo filter 7B. The extracted data are sent from the receiver unit 7 to the B-mode unit 30 and the color flow mapping unit 9.

The B-mode unit 30 is constituted by an envelope detection circuit 30A and a logarithmic converter 30B. The envelope detection circuit 30A detects the envelope of the output signals delivered from the echo filter 7B. The data thus detected is called "B-mode detection data". The logarithmic converter 30B subjects the B-mode detection data to a compression process based on logarithmic conversion. Incidentally, while the signals after the envelope detection and before the logarithmic conversion are called the "B-mode detection data" as stated above, data after the envelope detection and after the logarithmic conversion are sometimes called "B-mode raster data".

The color flow mapping unit 9 is constituted by a phase detection circuit, an analog-to-digital converter, an MTI filter, an autocorrelator and an arithmetic unit though not shown. This color flow mapping unit 9 extracts blood flow components based on the Doppler effect, and obtains blood flow information items, such as a mean velocity, a variance and power, at multiple points. The blood flow information items are sent to the display unit 21 through the CFM-mode DSC unit 10 as well as the memory composition unit 11, and are color-displayed as a mean velocity image, a variance image, a power image, and an image in which these images are combined.

The frame memory 12 stores the data of echo signal groups at individual processing stages (for example, RF data obtained after phasing addition, IQ data obtained after phase detection, B-mode detection data, B-mode raster data, and B-mode orthogonal transformation data obtained through orthogonal coordinate transformation by the B-mode DSC unit 8) every frame therein. The data can be read out of the frame memory 12 at any desired timing.

The control circuit 20 performs controls concerning the operation of the ultrasonic diagnostic equipment, especially a control concerning an ultrasonic image diagnosis based on intermittent transmission as will be stated later, as the control center of the whole system.

The blood-flow-index estimation unit 25 arithmetically estimates (or analyzes) an index about blood flow information, on the basis of echo signals obtained by ultrasound scans. Here, the "index about blood flow information" is the gradient (or rate) of the rise of intensity signals based on a TIC (Time Intensity Curve), a maximum-intensity arrival time, an MTT (Mean Transit Time), or the like.

The estimation of the index about blood flow information in the blood-flow-index estimation unit 25 proceeds as stated below. The blood-flow-index estimation unit 25 invokes a predetermined echo signal group stored in the frame memory 12, and calculates a mean value or the like representative value within an estimation area, on the basis of the intensities of echo signals at individual sample points. The representative value is the intensity (echo signal intensity) mean value, a maximum intensity value, a minimum intensity value, a most frequent intensity value, an intensity median, or any other statistical representative value concerning the intensities. By the way, in case of utilizing the signal group of the B-mode raster data, the B-mode orthogonal transformation data or the like subjected to the logarithmic conversion beforehand, a logarithmic inverse conversion process needs to be executed for restoring the data to the linear data, before calculating the representative value.

In accordance with a scan sequence to be stated later, an echo signal group before bubbles are broken by high-acoustic-pressure transmission is obtained as the maximum value by the above calculation. The blood-flow-index estimation unit 25 obtains the TIC by estimating a straight line or a curve in such a way that the rate of change of signal intensities versus time is fitted by a straight line approximation or a curve approximation on the basis of that change of the signal intensities between frames which has been found using the maximum value and an echo signal group obtained by low-acoustic-pressure transmission subsequent to the high-acoustic-pressure transmission. Besides, the blood-flow-index estimation unit 25 makes an analysis utilizing the TIC, thereby to calculate the index about blood flow information. The calculated index about blood flow information is stored in the frame memory 12 again. Incidentally, the scan sequence for obtaining the TIC is so constructed that scans by the low-acoustic-pressure transmission are performed a plurality of times in order to obtain index values at different times, and that the high-acoustic-pressure transmission is not performed during the scans by the low-acoustic-pressure transmission.

The B-mode digital scan converter (DSC) unit 8 and the CFM-mode digital scan converter (DSC) unit 10 convert the scan-line signal train of the ultrasound scans as inputted from the B-mode unit 30, into the data of an orthogonal coordinate system as based on spatial information. Video format conversion is performed in sending data from the memory composition unit 11 to the display unit 21.

The memory composition unit 11 composites character information items of various setting parameters, graduations, a guidance image to be stated later, or the like into one frame, and executes a process for converting the frame into the scan-line signal train of a general video format represented by television, so as to output a video signal to the display unit 21. Besides, in a TIC analysis process to be stated later, the memory composition unit 11 accepts the index about blood flow information from the frame memory 12 and composites the index with a background B-mode image in compliance with the request of the operator or the like, so as to display the resulting image in a predetermined form.

The display unit 21 displays morphological information within the living body and the blood flow information as an image. Besides, in the case of employing the contrast medium, the display unit 21 displays the spatial distribution of the contrast medium, that is, a region where a blood flow or blood exists, as an intensity image or a color image on the basis of a quantitative information content obtained. The frame memory 12 is included for storing the digital data output of the memory composition unit 11 therein.

The storage unit 27 is storage means in which an acoustic field V indicating the magnitude of a space for an acoustic pressure capable of causing micro bubbles to collapse and disappear is stored every depth D. Incidentally, the values of the acoustic field V are determined by previous measurements or simulations in which the parameters of ultrasounds transmitted from the probe 4, such as a frequency, a focusing point and an MI value, are controlled. The storage unit 27 may be in any form which can save and offer electronic data, such as a hard disk, FD, CD or MD.

(Quantitative Information Analyses)

Next, a series of quantitative information analyses which the ultrasonic diagnostic equipment makes will be described. Incidentally, a case of making a TIC analysis as the quantitative information analysis will be exemplified in this embodiment. Herein, a TIC analysis process is executed by the blood-flow-index estimation unit 25 on the basis of the control of the CPU 20. By the way, the quantitative information analysis may well be executed in an image processing apparatus which is incarnated by a workstation or a personal computer.

Figure 2:
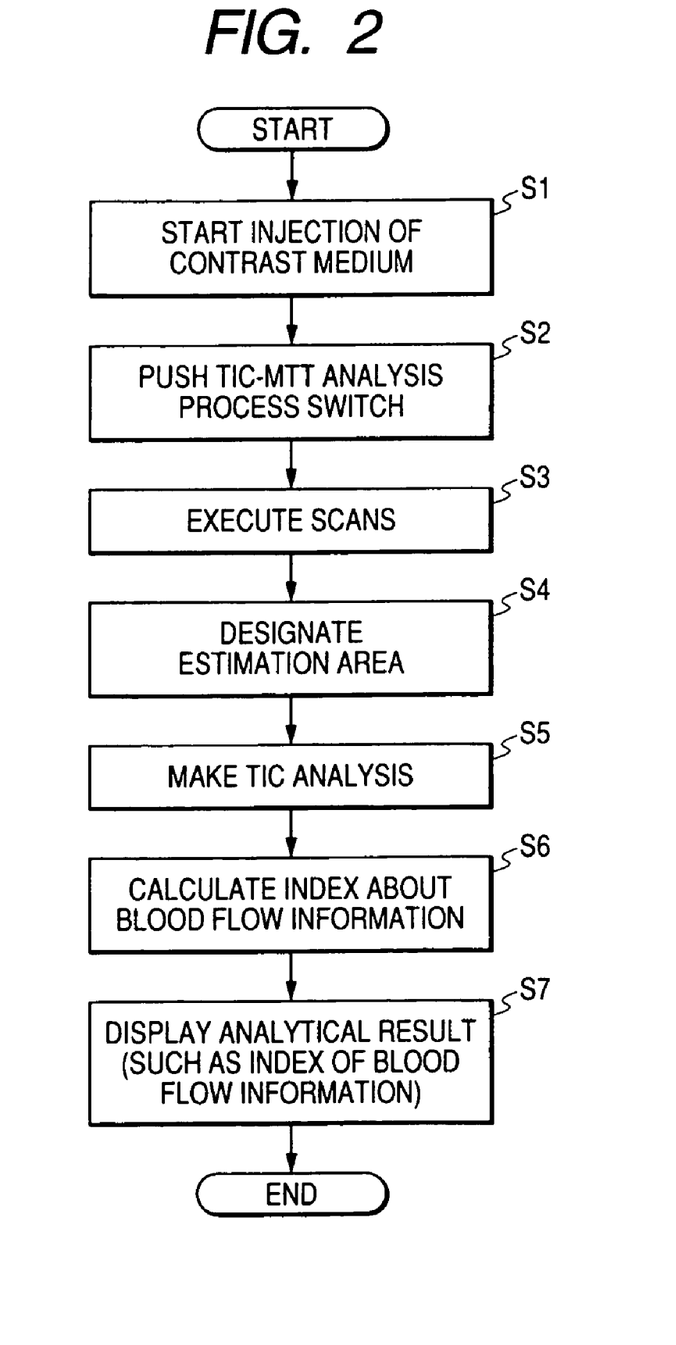
FIG. 2 is a flow chart showing the processing steps of a TIC analysis which the ultrasonic diagnostic equipment makes.

FIG. 2 is a flow chart showing the processing steps of the TIC analysis which the ultrasonic diagnostic equipment makes. Referring to FIG. 2, the injection of a (next-generation) contrast medium into the patient P is first started (step S1). The contrast medium is injected from a vein into blood continuously and slowly every predetermined amount.

Subsequently, while observing an ultrasound image which has been scanned in a scan mode based on ultrasounds under a low acoustic pressure or a medium acoustic pressure that does not break the contrast medium, the operator confirms that an object to-be-diagnosed (such as internal organ) has been sufficiently filled with the bubbles of the contrast medium. Then, the operator determines a section being a subject for the TIC analysis process and holds (or fixes) a probe at the section. Further, the operator requests the patient P to hold his/her breath and confirms that the motions of the object to-be-diagnosed have been suppressed. Thereafter, the operator pushes the start switch for starting regular scanning and the TIC analysis process (a time at which the switch was pushed will be denoted by $t_0$ below), thereby to start a scan sequence (step S2).

When the start switch has been pushed, the scanning based on the contrast echo method is executed (step S3). Since the next-generation contrast medium is used, scans conforming to a conventional sequence are not appropriate for the scanning. In the ultrasonic diagnostic equipment, scans are executed on the basis of a sequence as shown in FIG. 3 by way of example, in order to exploit the characteristics of the next-generation contrast medium to the utmost.

Figure 3:
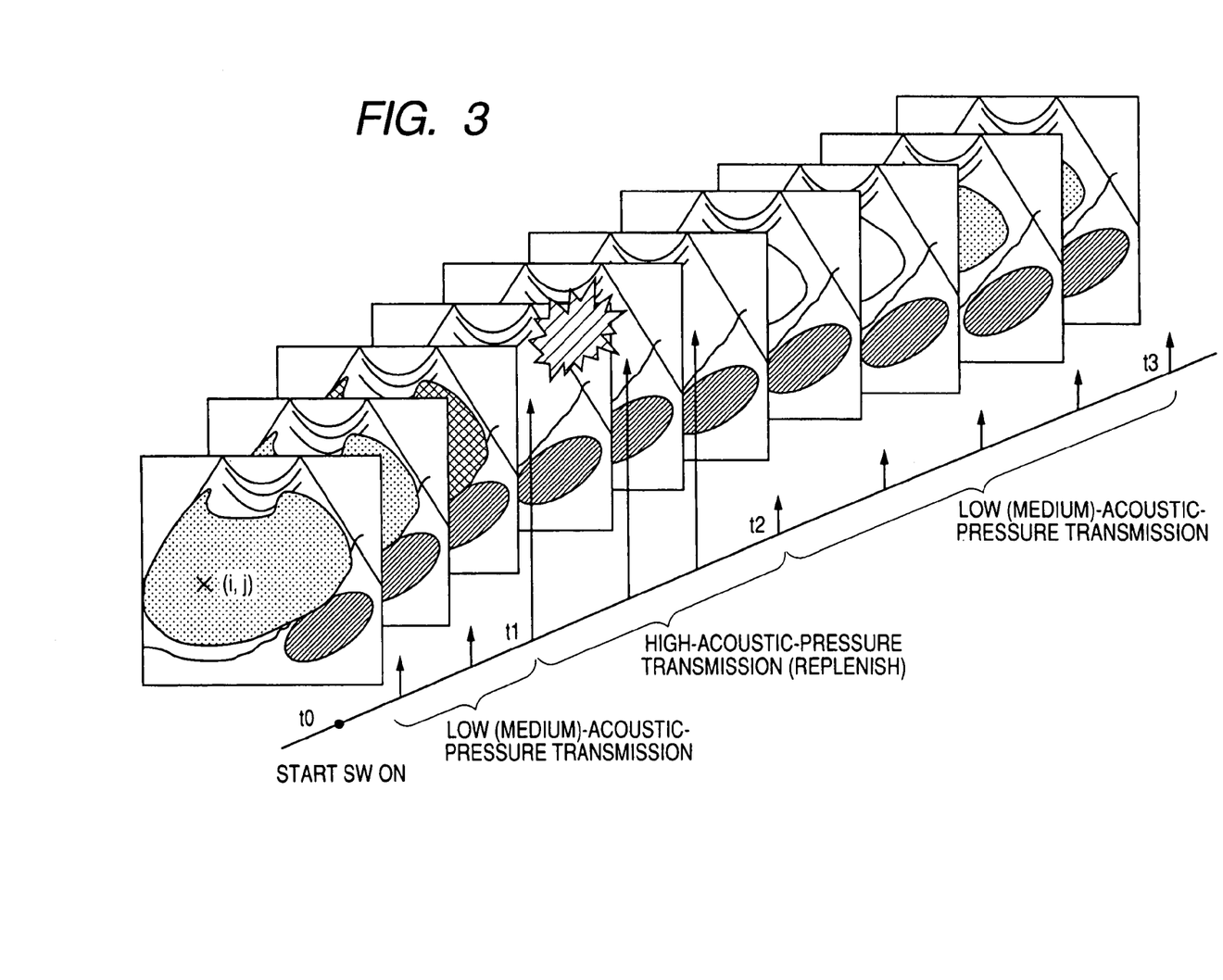
FIG. 3 is a diagram schematically showing the flow of scans since the push of a sequence start switch.

FIG. 3 is a diagram schematically showing the flow of scans since the push of the sequence start switch. As shown in the figure, the scans proceed in accordance with the following steps (1) through (3):

(1) In a time period from the time $t_0$ to a preset time $t_1$, scan is executed by ultrasounds under a low acoustic pressure or a medium acoustic pressure which does not break the contrast medium. Owing to the scan for the time period, echo signals in the case where the quantity of the contrast medium in the object to-be-diagnosed has reached a saturation value (maximum value) are collected. The intensities of the echo signals (harmonic components) obtained in the time period become a maximum value.

(2) In a time period from the time $t_1$ to a time $t_2$, scan (replenish scan) is executed by ultrasounds under a high acoustic pressure for the purpose of causing the contrast medium within the section to disappear and collapse and refreshing the section. Incidentally, the ultrasound scan in the time period should preferably be performed for at least one frame under a sufficiently high acoustic pressure in order to completely annihilate and break the contrast medium within the section.

(3) In a time period from the time $t_2$ to a preset time $t_3$, scan by ultrasounds under a low acoustic pressure or a medium acoustic pressure which does not break the contrast medium is executed from a state (at the time $t_2$) where the contrast medium within the section has been annihilated substantially completely. Owing to the scan in the time period, echo signals which are reflective of the quantity of the contrast medium flowing into the object to-be-diagnosed with the lapse of time are collected. Incidentally, the echo signals which are collected in the time period are, in general, proportional to the quantity of the inflow contrast medium.

Subsequently, a region which is desired to be estimated by the TIC measurement (hereinbelow, termed "estimation area") is designated for an ultrasound image displayed on the display unit 21 (step S4). The designation is done by an input from the mouse 13, the track ball 14 or the like of the operation panel 15.

Subsequently, the blood-flow-index estimation unit 25 calculates signal intensities (intensity values) in individual phases, on the basis of the echo signals collected in the time period $t_0$-$t_1$ and the time period $t_2$-$t_3$ at respective sample points on scan lines within the estimation area, and it plots the signal intensities on a coordinate plane in which the axis of ordinates represents the signal intensity, while the axis of abscissas represents a transmission time. Thus, the estimation unit 25 estimates a TIC shown in FIG. 4 by way of example and a gradient tan γ at the time $t_2$ as similarly shown in FIG. 5 (step S5). A recursive operation such as the method of least square can be used as a technique for the estimation.

Figure 4:
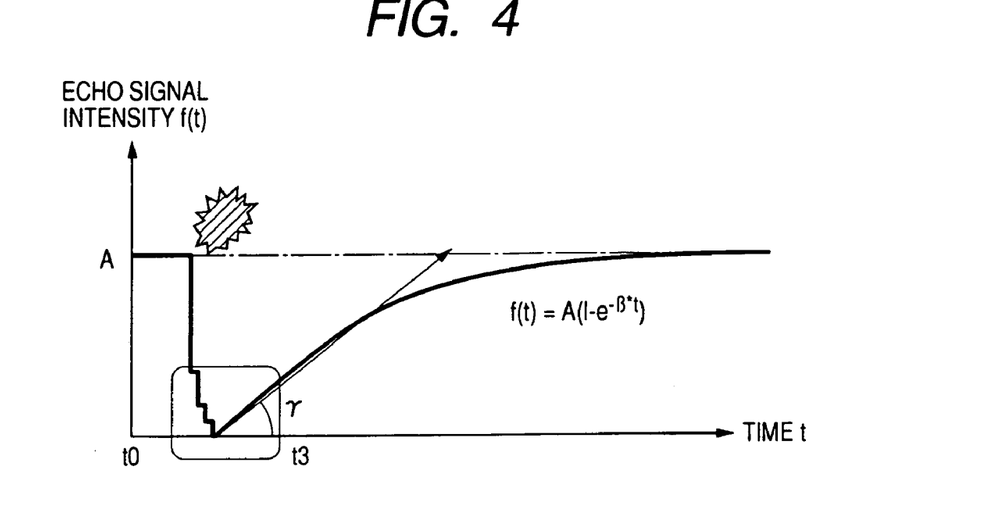
FIG. 4 is a diagram showing a TIC obtained by the TIC analysis process.
Figure 5:
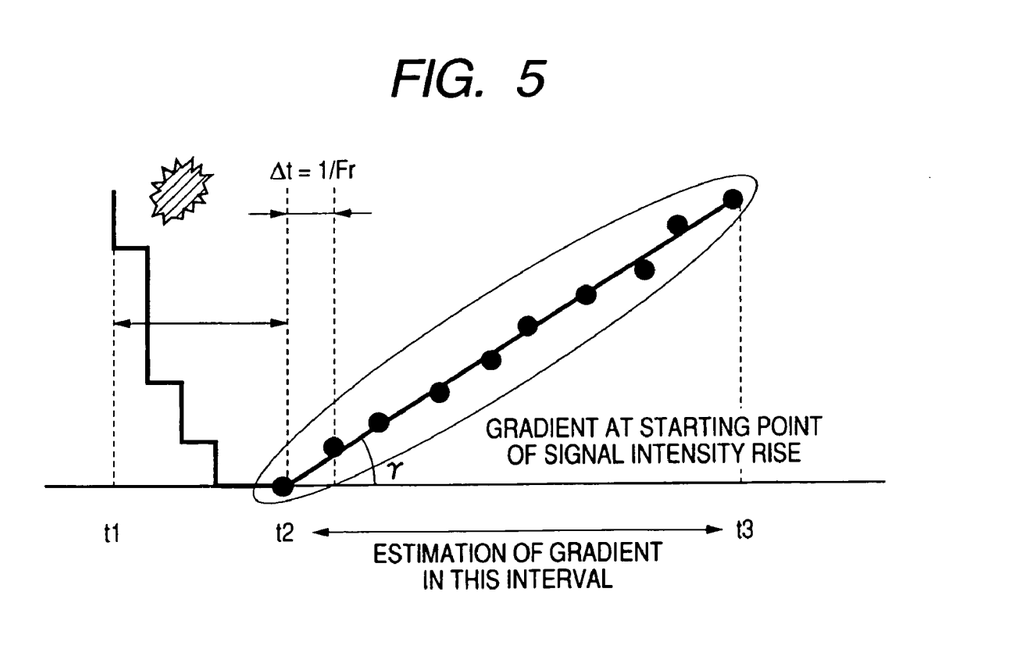
FIG. 5 shows an enlarged diagram corresponding to the time period $t_1$-$t_3$ of the TIC shown in FIG. 4.

Incidentally, FIG. 4 shows the TIC obtained by the analysis process, while FIG. 5 shows an enlarged diagram corresponding to the time period $t_1$-$t_3$ of the TIC shown in FIG. 4. In FIGS. 4 and 5, time periods and signs signify the following contents:

$t_0$-$t_1$: Echo signal group for acquiring and calculating the maximum value $t_1$-$t_2$: Replenish $t_2$-$t_3$: Signal group for calculating the rate of change for the intensity changes of echo signals (straight line or curve fitting)

A: Maximum intensity

Formula of a saturation process: $f(t)=A(1-\exp[-\beta t])$ f(t): Echo signal intensity γ: Gradient angle at the starting point of a signal intensity rise.

Subsequently, the blood-flow-index estimation unit 25 calculates, for example, the A-value (the maximum value or saturation value), a β-value (a value concerning the inflow velocity of the contrast medium), a mean transit time (MTT=A/tan γ), and time periods in which the echo signals arrive at values in proportions designated relative to the maximum value (including a maximum-value arrival time, etc.) based on the formula of the saturation process; $f(t)=A(1-\exp[-\beta t])$ by utilizing the signal groups which constitute the estimated TIC (step S6).

Figure 6:
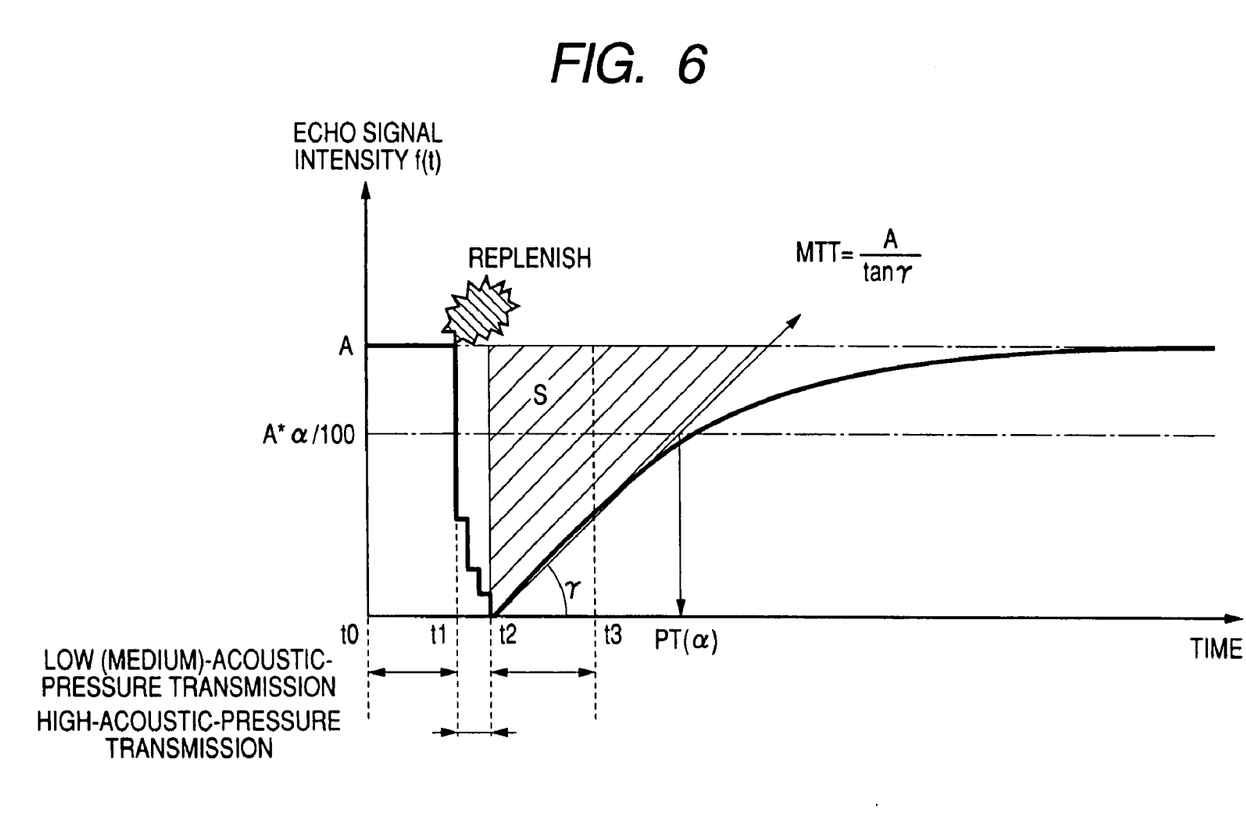
FIG. 6 is a diagram exemplifying a mean transit time and a designated-signal-intensity arrival time which are obtained by the TIC analysis process.

FIG. 6 is a diagram exemplifying the mean transit time and the designated-signal-intensity arrival time which are obtained by the TIC analysis process.

By the way, in FIG. 6, time periods and signs signify the following contents:

$t_0$-$t_1$: Echo signal group for acquiring and calculating the maximum value $t_1$-$t_2$: Replenish $t_2$-$t_3$: Signal group for calculating the rate of change for the intensity changes of echo signals (straight line or curve fitting)

A: Maximum intensity

Formula of a saturation process: $f(t)=A(1-\exp[-\beta t])$

S: Area defined including the time $t_2$, the maximum value $A_{ij}$ and an estimated straight line (or curve)

MTT: Mean transmit time

Pt(α): Time period in which an echo signal arrives at α% of the maximum intensity A of signals (maximum-value arrival time at α=100).

In the analysis process, the TIC concerning the object to-be-diagnosed is uniquely determined. Accordingly, when the TIC obtained is utilized, the time period Pt(α) can be known by inputting the desired proportion A·α/100 relative to the maximum value.

The clinical information Pt(α) may be presented to the operator in any scheme. Considered as the presenting scheme is, for example, a display scheme as will be explained at a step S7 in FIG. 2, or a scheme in which the analytical result exemplified in FIG. 6 is displayed on the display unit 21, and the operator brings a cursor to the position of the desired proportion A·α/100 relative to the maximum value on the axis of ordinates and then right-clicks, whereby the information Pt(α) corresponding to the proportion is displayed.

Subsequently, the blood flow information obtained by the TIC analysis process is presented to the operator (step S7). Regarding the presentation of the blood flow information, display methods to be explained below with reference to FIGS. 7 through 9 are effective by way of example.

Figure 7:
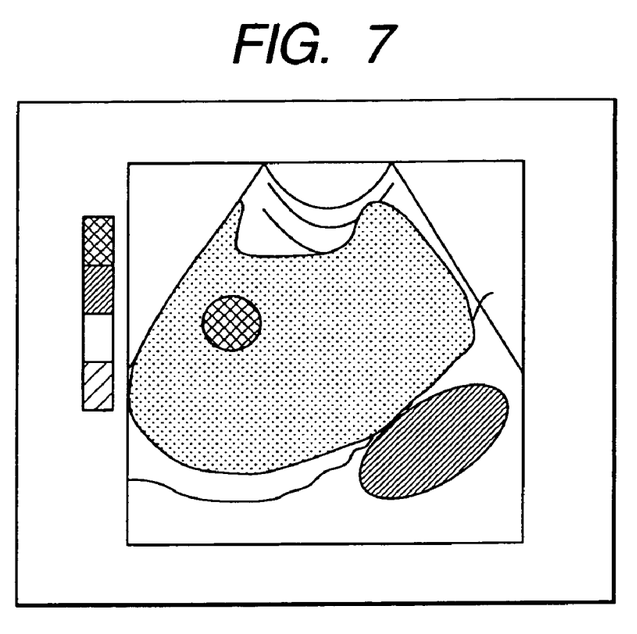
FIG. 7 is a diagram for explaining an example of a display method for blood flow information obtained by the TIC analysis process.

FIG. 7 shows an example in which the index (namely, TIC) of the blood flow information obtained at individual points is displayed as a two-dimensional mapping image (two-dimensional mapping display) by allotting colors (or intensities) in accordance with the values of the index. In this case, a color bar which indicates the relationship between the magnitudes of the index and the colors should preferably be displayed simultaneously with the two-dimensional mapping image so that the index magnitudes can be readily judged. Besides, if necessary, the final frame image by the high-acoustic-pressure ultrasounds employed in the data collection mode (that is, the final frame image obtained by the scan during the time period $t_1$-$t_2$) or the like tissue image, or any other frame image obtained by the scan sequence may well be composited with the two-dimensional mapping image and displayed as the background thereof.

Figure 8:
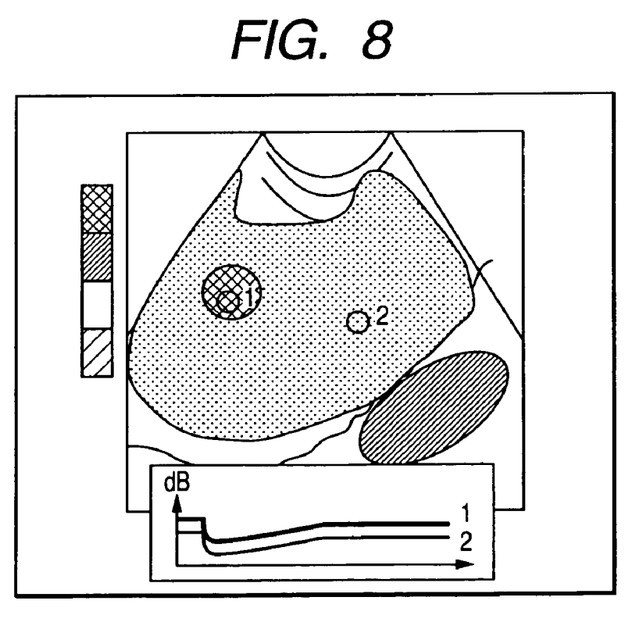
FIG. 8 is a diagram for explaining another example of the display method for the blood flow information obtained by the TIC analysis process.

FIG. 8 shows an example in which an ROI is set in a section being a subject for scanning and a TIC analysis process, and a two-dimensional mapping image concerning the ROI, as well as an intensity curve concerning the ROI is displayed. The intensity curve concerning the ROI is obtained in such a way that an ROI is further designated within the estimation area, and that the processing of the steps S5 through S7 is executed for this ROI. A plurality of such ROIs can be designated at desired positions as shown in FIG. 8. Besides, sample points may well be conjointly displayed.

Figure 9:
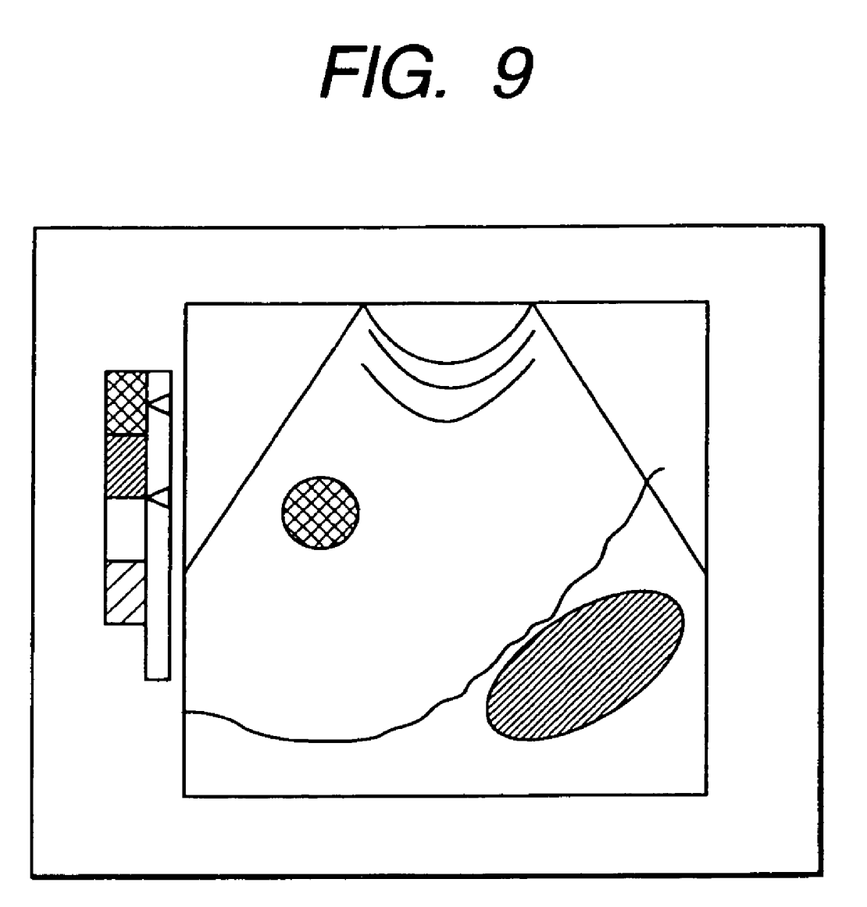
FIG. 9 is a diagram for explaining still another example of the display method for the blood flow information obtained by the TIC analysis process.

FIG. 9 shows an example in which, in the two-dimensional mapping display, only index values corresponding to a designated range in the color bar are displayed (filter display). Such a display scheme can selectively extract and indicate an area which has the index values in the specified range. Accordingly, in a case, for example, where the index is γ or tan γ corresponding to the inflow velocity of blood, the display scheme has the advantage that an artery-controlled malignant tumor part as to which the inflow velocity of a blood flow is said to be comparatively high can be extracted and indicated by an appropriate range designation.

Incidentally, in-vivo information to be mentioned below by way of example can also be analyzed by utilizing the information obtained by the TIC analysis.

Figure 10:
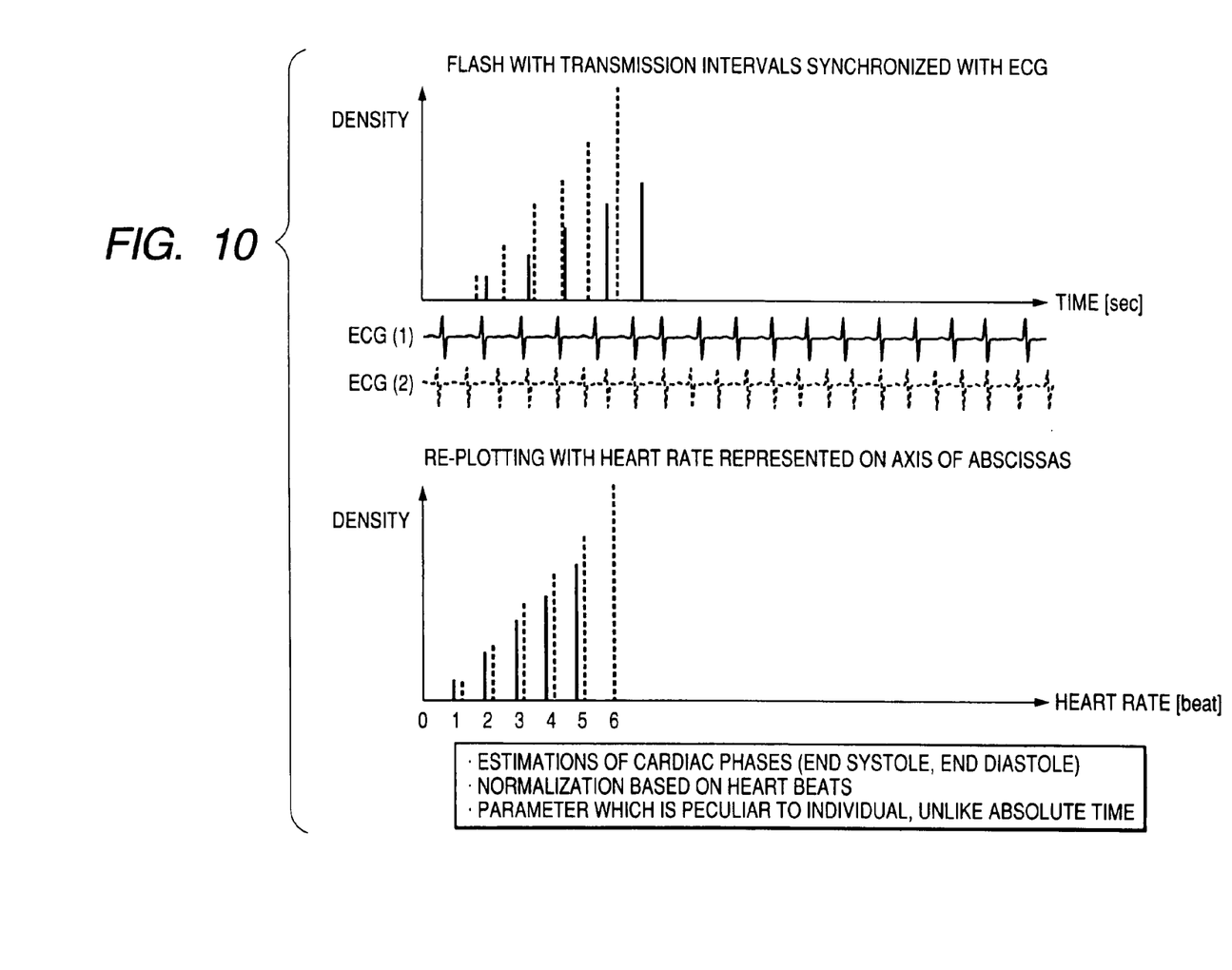
FIG. 10 is a diagram showing in-vivo information MTB (Mean Transit Beat) which can be analyzed by utilizing information obtained by the TIC analysis.

FIG. 10 is a diagram showing in-vivo information MTB (Mean Transit Beat) which can be analyzed by utilizing the information obtained by the TIC analysis. In the figure, the axis of ordinates represents the density, while the axis of abscissas represents the heart rate. The MTB may be measured in such a way that the processing of the same contents as already explained is executed for the steps S1 through S4 in FIG. 2, and that the typical values of respective images are plotted on a coordinate plane representing the density on the axis of ordinates and the heart rate on the axis of abscissas, on the basis of signals measured by the ECG 1 at the step S5.

Since the MTB is normalized on the basis of heart beats, it can be a parameter which is peculiar to an individual, unlike the absolute time. As the advantage of the MTB, accordingly, it is possible to expect the effect of eliminating the different influences of the ages and figures of individuals on the heart rate, in the estimations of predetermined cardiac phases (for example, end systole and end diastole).

As described above, according to the ultrasonic diagnostic equipment of this embodiment, after the pervasion of the contrast medium over the scan section has been confirmed by the low-acoustic-pressure scan or medium-acoustic-pressure scan which does not burst the bubbles, the scan under the high acoustic pressure which breaks the bubbles is performed, so as to refresh the section and to acquire the maximum value of echo signal intensities. Subsequently, the scans employing the ultrasounds under the low acoustic pressure or medium acoustic pressure which does not break the contrast medium are carried out the plurality of times at the different timings, thereby to execute the scan sequence for acquiring the in-vivo information necessary for the TIC analysis. According to the sequence, the acquisition of the information which is, at least, necessary for the TIC analysis requires only the time period in which the contrast medium falls into a saturation state, and the time period which is expended since the contrast medium breaking by the high-acoustic-pressure scan, till the completion of the ultrasound scans under the low acoustic pressure or medium acoustic pressure that does not break the contrast medium.

Assuming by way of example that a field of view be 15 cm in the abdominal region, the scans under the low acoustic pressure or medium acoustic pressure can be continuously performed in the ultrasonic diagnostic equipment, and hence, a frame rate becomes about 15, though this depends upon conditions. Consequently, regarding the number of data for estimating a TIC, at sample points on each scan line, there are nearly 45 time series data even when the time period $t_2$-$t_3$ is assumed to be 3 seconds. Accordingly, the large number of time series data can be employed in the shorter time than in the prior-art intermittent transmission, and an estimation precision can also be heightened. Besides, in a case where the time period $t_0$-$t_1$ for obtaining the maximum value is set at one second, the data of 15 frames can be collected in the above example. Accordingly, the precision of the maximum value can also be heightened by taking a mean value. In this case, when the total scan time period is assumed to be 5 seconds, a breath holding period may be short, and a burden on the person to-be scanned is lightened.

In this manner, according to the ultrasonic diagnostic equipment, it is possible to perform the contrast echo examination which satisfactorily exploit the characteristics of the next-generation contrast medium that it is not broken by the ultrasound of the low acoustic pressure or medium acoustic pressure. Accordingly, the ultrasound scan time period can be made shorter than in the prior art, and a section holding time period and a breath holding time period may be short. As a result, burdens on the operator and the person to-be-scanned can be lightened. Further, owing to the data collection for the short time, influences ascribable to the motions of internal organs can be relieved, and the larger number of time series data than in the prior art can be employed. Consequently, the estimation precision can be enhanced. Moreover, since the bubbles do not continue to be burst as in the case of the conventional contrast medium, data can be collected many times.

Besides, according to the ultrasonic diagnostic equipment, when the operator manipulates the switch of the operation panel at a desired timing, the above scan sequence can be automatically started at a predetermined timing in accordance with a prestored program. Accordingly, the operator can perform the contrast echo examination satisfactorily exploiting the characteristics of the next-generation contrast medium, quickly by the simple manipulation, with the result that the burden of the job on the operator can be lightened.

Further, according to the ultrasonic diagnostic equipment, the blood flow information obtained by the TIC analysis process can be displayed in such a scheme as the two-dimensional mapping display, the two-dimensional mapping display concerning the ROI or ROIs and the intensity curve display, or the filter display. Accordingly, the observer can quickly observe the obtained blood flow information in the desired scheme easy of understanding.

Second Embodiment

In the first embodiment already described, $f(t)=A(1-\exp[-\beta t])$ was adopted as the formula indicative of the saturation process, and the time periods in which the A-value, the $\beta$-value and the mean-transit-time echo signals reached the values of the proportions designated relative to the maximum values were calculated on the basis of the formula.

On the other hand, in the second embodiment, $f(t)=A(1-B\cdot\exp[-\beta t])$ is adopted as a more general formula indicative of the saturation process, and the A-value, etc. are computed on the basis of this formula. Incidentally, letter B denotes an intensity change contribution rate which is determined in accordance with predetermined conditions, and which is a desired parameter.

Methods for determining the intensity change contribution rate B are as stated below. By way of example, the value of the parameter B is changed, and the B value which minimizes the cumulative absolute-value error or cumulative squared error between values calculated by the formula $f(t)=A(1-B\cdot\exp[-\beta t])$ and the values of actually measured sample points (that is, the B value which affords the highest reliability of a statistical estimation value) can be determined as the value of the parameter B. Alternatively, the peculiar value of the parameter B may well be determined in correspondence with, for example, a part to-be-diagnosed or a set ROI on clinical grounds. Further, for the purpose of finely adjusting the formula $f(t)=A(1-B\cdot\exp[-\beta t])$, the value of the parameter B may well be determined in such a way that an operator selects the B value from within the pre-created table of B values by a manual operation. Such a process for determining the parameter B is executed at the calculation processing of the index about blood flow information (at the step S6 in FIG. 2) by, for example, the blood-flow-index estimation unit 25 (in FIG. 1).

According to the configuration described above, a quantitative information analysis of still higher precision can be quickly and readily realized in addition to the advantages stated as to the first embodiment.

By the way, the present invention is not restricted to the embodiments as they are, but it can incarnate ultrasonic diagnostic equipments by modifying the constituents at the stage of performance within a scope not departing from the purport of the invention. Moreover, various contrivances can be made by appropriately combining the plurality of constituents mentioned in the embodiments. By way of example, some of all the constituents mentioned in each of the embodiments may well be omitted. Furthermore, the constituents included in the different embodiments may well be appropriately combined.

What is claimed is:

1. An ultrasonic diagnostic equipment, comprising:
   an ultrasonic probe configured to transmit and receive ultrasounds to and from a subject for scanning within a patient given a contrast medium;
   a drive unit configured to generate a drive signal for driving said ultrasonic probe, and to feed the drive signal to the ultrasonic probe;
   a control unit configured to control said drive unit on the basis of a sequence for collecting changes-versus-time of a contrast medium density within the subject for scanning, the sequence being formed so that, after the contrast medium flowing into the subject for scanning has substantially fallen into a saturation state, first ultrasounds at an intensity at which the contrast medium is broken are transmitted from said ultrasonic probe, and that, after the transmission of the first ultrasounds, second ultrasounds at an intensity at which the contrast medium is not broken are transmitted from said ultrasonic probe at least twice;
   an analysis unit configured to analyze a blood flow of the subject for scanning, on the basis of ultrasonic echoes received in correspondence with at least two transmissions of the second ultrasounds by the ultrasonic probe, and to estimate information with respect to the blood flow of the subject after the at least two transmissions of the second ultrasounds are executed; and
   a display unit configured to display the information on the blood flow of the subject.

2. An ultrasonic diagnostic equipment as defined in claim 1, further comprising:
   an instruction unit through which an instruction of starting the ultrasound scans conforming to the sequence is given;
   wherein said control unit is configured to start the control of said drive unit based on the sequence, in response to the instruction from said instruction unit.

3. An ultrasonic diagnostic equipment as defined in claim 1, further comprising:
   a setting unit configured to set at least either a transmission timing of the first ultrasounds or transmission timings of the second ultrasounds;
   wherein said control unit is configured to control said drive unit so that at least either of the first ultrasounds or the second ultrasounds may be transmitted at the timing or timings set by said setting unit.

4. An ultrasonic diagnostic equipment as defined in claim 1, wherein the information on the blood flow of the subject for scanning includes at least one member selected from the group consisting of an A-value, a β-value, a product value between the A-value and the β-value, a time period in which a signal intensity reaches a predetermined proportion relative to a signal-intensity maximum value, and a mean transit time, based on a formula $f(t)=A(1-\exp[-\beta t])$ where symbol $f(t)$ denotes an intensity, letter A denotes the maximum intensity, and letter t denotes time.

5. An ultrasonic diagnostic equipment as defined in claim 1, wherein:
   the information on the blood flow of the subject for scanning includes at least one member selected from the group consisting of a mean intensity value, a maximum intensity value, a minimum intensity value, a most frequent intensity value, an intensity median, and any other statistical representative value concerning intensity values, for sample points which exist within the subject for scanning; and
   said display unit displays the information on the blood flow of the subject for scanning in such a way as to indicate any of numerical values, a table, or a time intensity curve.

6. An ultrasonic diagnostic equipment as defined in claim 1, wherein:
   the information on the blood flow of the subject for scanning includes at least one member selected from the group consisting of a mean intensity value, a maximum intensity value, a minimum intensity value, a most frequent intensity value, an intensity median, and any other statistical representative value concerning intensity values, for sample points which exist within the subject for scanning; and
   said display unit generates and displays a two-dimensional mapping image which is obtained by allotting to the sample points, colors that correspond to magnitudes of the statistical representative value concerning the intensity values.

7. An ultrasonic diagnostic equipment as defined in claim 6, wherein said display unit generates the two-dimensional mapping image on the basis of only those sample points within the subject for scanning which belong to a designated range, among the sample points of the statistical representative value.

8. An ultrasonic diagnostic equipment as defined in claim 1, further comprising:
   a region-of-interest setting unit configured to set a region of interest on the subject for scanning;
   wherein said analysis unit is configured to analyzes the blood flow of the region of interest, on the basis of the ultrasonic echoes received by said ultrasonic probe.

9. An ultrasonic diagnostic equipment as defined in claim 1, wherein:
   the information on the blood flow of the region of interest includes at least one member selected from the group consisting of a mean intensity value, a maximum intensity value, a minimum intensity value, a most frequent intensity value, an intensity median, and any other statistical representative value concerning intensity values, for the region of interest; and
   said display unit displays the information on the blood flow of the region of interest in such a way as to indicate any of numerical values, a table, or a time intensity curve.

10. An ultrasonic diagnostic equipment as defined in claim 8, wherein:
    the information on the blood flow of the region of interest includes at least one member selected from the group consisting of a mean intensity value, a maximum intensity value, a minimum intensity value, a most frequent intensity value, an intensity median, and any other statistical representative value concerning intensity values, for the region of interest; and
    said display unit generates and displays a two-dimensional mapping image which is obtained by allotting colors that correspond to magnitudes of the statistical representative value concerning the intensity values of the region of interest.

11. An ultrasonic diagnostic equipment as defined in claim 10, wherein said display unit generates the two-dimensional mapping image on the basis of only those sample points within the subject for scanning which belong to a designated range, among sample points of the statistical representative value.

12. An ultrasonic diagnostic equipment as defined in claim 1, wherein the information on the blood flow of the subject for scanning includes at least one member selected from the group consisting of an A-value, a β-value, a product value between the A-value and the β-value, a time period in which a signal intensity reaches a predetermined proportion relative to a signal-intensity maximum value, and a mean transit time, based on a formula $f(t)=A(1-B\cdot\exp[-\beta t])$ where symbol $f(t)$ denotes an intensity, letter A denotes the maximum intensity, letter B denotes an intensity change contribution rate, and letter t denotes time.

13. An image processing apparatus, comprising:
a memory which stores therein echo signals obtained in accordance with a scan sequence for collecting changes-versus-time of a contrast medium density within a subject for scanning inside a patient, the scan sequence being formed so that, after a contrast medium flowing into the subject for scanning has substantially fallen into a saturation state, first ultrasounds at an intensity at which the contrast medium is broken are transmitted, and that, at different timings after the transmission of the first ultrasounds, second ultrasounds at an intensity at which the contrast medium is not broken are transmitted at least twice;
an analysis unit configured to analyze a blood flow of the subject for scanning, on the basis of the echo signals which are stored in said memory and received in correspondence with at least two transmissions of the second ultrasounds, and to estimate information with respect to the blood flow of the subject after the at least two transmissions of second ultrasounds are executed; and
a display unit configured to display the information on the blood flow of the subject.

14. An image processing apparatus as defined in claim 13, wherein the information on the blood flow of the subject for scanning includes at least one member selected from the group consisting of an A-value, a β-value, a product value between the A-value and the β-value, a time period in which a signal intensity reaches a predetermined proportion relative to a signal-intensity maximum value, and a mean transit time, based on a formula $f(t)=A(1B\cdot\exp[-\beta t])$ where symbol $f(t)$ denotes an intensity, letter A denotes the maximum intensity, letter B denotes an intensity change contribution rate, and letter t denotes time.

15. An image processing apparatus as defined in claim 13, wherein the information on the blood flow of the subject for scanning includes at least one member selected from the group consisting of an A-value, a β-value, a product value between the A-value and the β-value, a time period in which a signal intensity reaches a predetermined proportion relative to a signal-intensity maximum value, and a mean transit time, based on a formula $f(t)=A(1-\exp[-\beta t])$ where symbol $f(t)$ denotes an intensity, letter A denotes the maximum intensity, and letter t denotes time.

16. An image processing apparatus as defined in claim 13, wherein:
the information on the blood flow of the subject for scanning includes at least one member selected from the group consisting of a mean intensity value, a maximum intensity value, a minimum intensity value, a most frequent intensity value, an intensity median, and any other statistical representative value concerning intensity values, for sample points which exist within the subject for scanning; and
said display unit displays the information on the blood flow of the subject for scanning in such a way as to indicate any of numerical values, a table, or a time intensity curve.

17. An image processing apparatus as defined in claim 13, wherein:
the information on the blood flow of the subject for scanning includes at least one member selected from the group consisting of a mean intensity value, a maximum intensity value, a minimum intensity value, a most frequent intensity value, an intensity median, and any other statistical representative value concerning intensity values, for sample points which exist within the subject for scanning; and
said display unit generates and displays a two-dimensional mapping image which is obtained by allotting to the sample points, colors that correspond to magnitudes of the statistical representative value concerning the intensity values.

18. An image processing apparatus as defined in claim 17, wherein said display unit generates the two-dimensional mapping image on the basis of only those sample points within the subject for scanning which belong to a designated range, among the sample points of the statistical representative value.

19. An image processing apparatus as defined in claim 13, further comprising:
a region-of-interest setting unit configured to set a region of interest on the subject for scanning;
wherein said analysis unit is configured to analyze the blood flow of the region of interest, on the basis of the echo signals stored in said memory.

20. An image processing apparatus as defined in claim 13, wherein:
the information on the blood flow of the region of interest includes at least one member selected from the group consisting of a mean intensity value, a maximum intensity value, a minimum intensity value, a most frequent intensity value, an intensity median, and any other statistical representative value concerning intensity values, for the region of interest; and
said display unit displays the information on the blood flow of the region of interest in such a way as to indicate any of numerical values, a table, or a time intensity curve.

21. An image processing apparatus as defined in claim 20, wherein:
the information on the blood flow of the region of interest includes at least one member selected from the group consisting of a mean intensity value, a maximum intensity value, a minimum intensity value, a most frequent intensity value, an intensity median, and any other statistical representative value concerning intensity values, for the region of interest; and
said display unit generates and displays a two-dimensional mapping image which is obtained by allotting colors that correspond to magnitudes of the statistical representative value concerning the intensity values of the region of interest.

22. An image processing apparatus as defined in claim 21, wherein said display unit generates the two-dimensional mapping image on the basis of only those sample points within the subject for scanning which belong to a designated range, among sample points of the statistical representative value.

23. An ultrasonic diagnostic equipment as defined in claim 1, wherein the at least two transmissions of the second ultrasounds are executed before the saturation state of the contrast medium is established.

24. An ultrasonic diagnostic equipment as defined in claim 1, wherein the at least two transmissions of the second ultrasounds are executed in 3 seconds.

25. An ultrasonic diagnostic equipment as defined in claim 1, wherein the at least two transmissions of the second ultrasounds are executed in a period when the changes-versus-time of the contrast medium density is substantially linear.

26. An ultrasonic diagnostic equipment as defined in claim 1, wherein the at least two transmissions of the second ultrasounds are executed after the transmission of the first ultrasounds and in a period which is shorter than a period establishment of the saturation state with respect to the changes-versus-time of the contrast medium density.

27. The ultrasonic diagnostic equipment of claim 1, wherein the analysis unit is configured to estimate information that indicates a time required to reach a predetermined echo intensity after the at least two transmissions of the second ultrasounds are executed.

* * * * *